US006685919B2

(12) United States Patent
Leinen et al.

(10) Patent No.: US 6,685,919 B2
(45) Date of Patent: *Feb. 3, 2004

(54) PLAQUE-CONTROLLING LIQUID TOOTH CLEANING GEL

(75) Inventors: Hans-Theo Leinen, Duesseldorf (DE); Dorothea Gregori, Neuss (DE); Peter Wuelknitz, Leichlingen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,410

(22) Filed: Oct. 11, 2002

(65) Prior Publication Data

US 2003/0118522 A1 Jun. 26, 2003

Related U.S. Application Data

(63) Continuation of application No. PCT/EP01/03697, filed on Mar. 31, 2001.

(30) Foreign Application Priority Data

Apr. 11, 2000 (DE) .......................................... 100 17 998

(51) Int. Cl.[7] .................................................. A61K 7/16
(52) U.S. Cl. ......................................................... 424/49
(58) Field of Search .................................... 424/49–88

(56) References Cited

U.S. PATENT DOCUMENTS

| 2,837,463 A | | 6/1958 | Fosdick et al. | |
| 3,538,230 A | | 11/1970 | Pader et al. | |
| 4,067,746 A | | 1/1978 | Wason et al. | |
| 4,108,978 A | * | 8/1978 | Mazzanobile | 424/49 |
| 4,153,680 A | | 5/1979 | Seybert | |
| 4,435,380 A | * | 3/1984 | Pader | 424/49 |
| 4,774,078 A | | 9/1988 | Curtis et al. | |
| 4,795,628 A | | 1/1989 | Afseth | |
| 4,857,289 A | | 8/1989 | Nauroth et al. | |
| 4,891,211 A | * | 1/1990 | Winston | 424/49 |
| 4,943,429 A | * | 7/1990 | Winston et al. | 424/49 |
| 5,178,869 A | * | 1/1993 | Ebine et al. | 424/49 |
| 5,456,745 A | * | 10/1995 | Roreger et al. | 106/128 |
| 5,622,168 A | * | 4/1997 | Keusch et al. | 252/500 |
| 5,628,985 A | * | 5/1997 | Stiller et al. | 424/49 |
| 5,858,333 A | * | 1/1999 | Winston et al. | 424/49 |
| 6,342,205 B1 | * | 1/2002 | Niemi et al. | 424/49 |
| 6,506,366 B1 | * | 1/2003 | Leinen et al. | 424/49 |

FOREIGN PATENT DOCUMENTS

| DE | 21 34 862 | 1/1973 |
| DE | 25 22 486 | 11/1975 |
| DE | 28 29 037 A1 | 1/1980 |
| DE | 31 14 493 | 10/1982 |
| DE | 37 29 401 A1 | 4/1988 |
| EP | 0 229 375 A1 | 7/1987 |
| EP | 0 408 174 A1 | 1/1991 |
| FR | 2 150 914 | 4/1973 |
| GB | 1 349 373 | 4/1974 |
| GB | 2 001 526 A | 2/1979 |

* cited by examiner

*Primary Examiner*—Shep K. Rose
(74) *Attorney, Agent, or Firm*—Stephen D. Harper; Gregory M. Hill

(57) ABSTRACT

A water based liquid tooth cleaning gel is presented with a viscosity below 50 Pa·s (20° C.) comprising

| 10–20% by weight of | a silica polish |
| 40–60% by weight of | a humectant selected from the group consisting of sorbitol, glycerol, polyethylene glycol and mixtures thereof, |
| 0.01 to 0.2% by weight of | magnesium in the form of a dissolved salt and |
| 0.01 to 1% by weight of | an antimicrobial 5-aminohexahydropyrimidine |

9 Claims, No Drawings

PLAQUE-CONTROLLING LIQUID TOOTH CLEANING GEL

CROSS REFERENCE TO RELATED APPLICATIONS

This application is a continuation under 35 U.S.C. §365 (c) and §120 of International Application No. PCT/EP01/03697 filed Mar. 31, 2001 and under §119 of German Patent Application No. 100 17 998.3 filed Apr. 11, 2000.

SUMMARY OF THE INVENTION

This invention relates to liquid tooth cleaning preparations containing polishes, humectants and water which contain an antimicrobial 5-aminohexahydropyrimidine as a tartar-inhibiting component.

BACKGROUND OF THE INVENTION 1,3-bis-(2-ethylhexyl)-5-methyl-5-aminohexahydropyrimidine is known as an antiseptic component by the name of hexetidine in oral hygiene and dental care preparations, for example from patent applications GB 2 001 526 A1, EP 0 229 375 A1, DE 3729401 A1 and EP 0 408 174 A1.

However, the prior art literature cited above does not disclose a liquid tooth cleaning preparation which contains this tartar-inhibiting component in a formulation containing polishing agents. The production of liquid tooth cleaning preparations with polishing components dispersed therein imposes stringent demands on the stability of such systems against sedimentation. Another problem is to incorporate tartar-inhibiting agents in such preparations without affecting transparency or the effectiveness of those agents. Finally, tooth cleaning preparations of the type in question are also supposed to contain other components to counteract the demineralization of dental enamel.

DESCRIPTION OF THE INVENTION

The present invention relates to a water-based liquid tooth cleaning gel with a viscosity below 50 Pa·s (20° C.), characterized by a content of

| | |
|---|---|
| 10 to 20% by weight of | a silica polish, |
| 40 to 60% by weight of | a humectant selected from sorbitol, glycerol, polyethylene glycol and mixtures thereof, |
| 0.01 to 0.2% by weight of | magnesium in the form of a dissolved salt and |
| 0.01 to 1% by weight of | an antimicrobial 5-aminohexahydropyrimidine |

Liquid in the context of the present invention means a viscosity of less than 40 mPa·s (as measured at 20° C. with a Brookfield RVF rotational viscosimeter, spindle ¾ at 4 r.p.m. corresponding to a shear rate D of 4 $S^{-1}$) which provides for dispensing from a small flexible bottle by light pressure and ensures that the gel sinks slowly into the bristles of the toothbrush.

The tooth cleaning gels according to the invention preferably also have a certain transparency. The transparency and viscosity according to the invention are achieved through the choice and quantity of the polishing components, thickeners and humectants used. It has been found that the transparency of the compositions is improved by the content of the magnesium salt. In addition, the magnesium salt makes a valuable contribution to the remineralizing effect of the tooth cleaning gel.

Suitable silica polishing components are any silica gels, silica hydrogels and precipitated silicas known as polishes. Silica gels are obtained by reacting sodium silicate solutions with strong aqueous mineral acids to form a hydrosol, ageing to form the hydrogel, washing and drying. If drying is carried out under moderate conditions to a water content of 15 to 35% by weight, the so-called silica hydrogels known, for example, from U.S. Pat. No. 4,153,680 are obtained. Drying to water contents below 15% by weight results in irreversible shrinkage of the previously loose structure of the hydrogel to the dense structure of the so-called xerogel. Silica xerogels are described, for example, in U.S. Pat. No. 3,538,230.

A second particularly suitable group of silica polishing agents are the precipitated silicas. Precipitated silicas are obtained by precipitation of silica from dilute alkali metal silicate solutions by addition of strong acids under conditions which preclude aggregation to the sol and gel. Suitable processes for the production of precipitated silicas are described, for example, in DE-OS 25 22 486 and in DE-OS 31 14 493. A particularly suitable precipitated silica is that produced in accordance with DE-OS 31 14 493 which has a BET surface of 15 to 110 $m^2/g$, a particle size of 0.5 to 20 $\mu m$ (at least 80% by weight of the primary particles should be below 5 $\mu m$ in size) and a viscosity in the form of a 30% glycerol/water (1:1) dispersion of 30 to 60 Pa.s (20° C.) and which is used in a quantity of 10 to 20% by weight, based on the tooth gel. In addition, particularly suitable precipitated silicas of this type have rounded corners and edges and are commercially obtainable under the name of Sident®12 DS (DEGUSSA). Another suitable silica is Zeodent 113 (Huber Corp.) with a BET surface of 150 to 250 $m^2/g$.

Other precipitated silicas of this type are Sident 8 (DEGUSSA) and Sorbosil AC 39 (Crosfield Chemicals). These silicas are distinguished by a weaker thickening effect and a slightly larger mean particle size of 8 to 14 $\mu m$ for a specific BET surface of 40 to 75 $m^2/g$ and are particularly suitable for liquid tooth gels according to the present invention.

Other polishes, particularly those which are detrimental to the transparency of the compositions but which, even in small amounts, considerably increase cleaning performance may optionally be present in quantities of less than 2% by weight. Such polishing components are, for example, pumice, zirconium silicate or gamma-aluminium oxide.

Of crucial importance to the rheology and transparency of the liquid tooth cleaning gels according to the invention is the composition of the liquid carrier phase of water and humectants. The total quantity of 40 to 60% by weight of the humectant combination is based on the tooth cleaning gel as a whole and consists essentially of sorbitol, glycerol and polyethylene glycol. Suitable polyethylene glycols are both low molecular weight and high molecular weight polyethylene glycols, i.e. those with average molecular weights of 200 to 10,000.

Where large amounts of sorbitol and small amounts of glycerol are used, a relatively high molecular weight polyethylene glycol should generally be employed. In a preferred embodiment, the humectants sorbitol (a), glycerol (b) and polyethylene glycol (c) are present in the tooth cleaning gels according to the invention in a ratio by weight of (a) to (b) to (c) of 10:(0–8):(0.2–2).

The water content of the tooth cleaning gels according to the invention is in the range from 25 to 35% by weight and is the sum of the quantities of water introduced by the raw materials, such as the 70% sorbitol or the 86% glycerol for example, and the quantities separately added. The quantities of sorbitol and glycerol mentioned are based on water-free active substances.

Suitable water-soluble magnesium salts are both inorganic salts such as, for example, $MgCl_2$, $MgF_2$, $MgSO_4$ and hydrates thereof and organic magnesium salts such as, for example, the magnesium salt of glycerophosphoric acids (magnesium glycerophosphate), glycolic acid, lactic acid, citric acid, gluconic acid, glutamic acid or aspartic acid. Magnesium is preferably used in the form of $MgSO_4.7H_2O$.

Suitable antimicrobial 5-aminohexahydropyrimidines are known, for example, from U.S. Pat. No. 2,837,463. A product particularly suitable for use in dental care preparations is 1,3-bis-(2-ethylhexyl)-5-methyl-5-aminohexahydropyrimidine which is also known by the name of hexetidine. For incorporation in the tooth cleaning gels according to the invention, the 5-aminohexahydropyrimidines may be used in free form or even in the form of their soluble salts, for example the sulfates, chlorides, fluorides, hydrogen phosphates, lactates, glycolates, citrates or salts of organopolyphosphonic acids, for example 1-hydroxyethane-1,1-diphosphonic acid or azacycloheptane-2,2-diphosphonic acid. The only requirement is that at least 0.01% by weight of the 5-aminohexahydropyrimidine should be present in dissolved form in the composition.

In addition to the compulsory components mentioned, the tooth cleaning gels according to the invention may contain 1 to 10% by weight of other toothpaste ingredients. Such ingredients are, for example, binders, surfactants, flavors and sweeteners, scale inhibitors, fluorine compounds, vitamins, panthenol and other active substances.

Suitable binders are, for example, natural and/or synthetic water-soluble polymers, such as alginates, carrageenates, tragacanth, starch and starch ethers, cellulose ethers such as, for example, carboxymethyl cellulose (Na salt), hydroxyethyl cellulose, methyl hydroxypropyl cellulose, guar, acacia gum, agar agar, xanthan gum, succinoglycan gum, locust bean gum, pectins, water-soluble carboxyvinyl polymers (for example Carbopol® types), polyvinyl alcohol, polyvinyl pyrrolidone, polyethylene glycols, more particularly those with molecular weights of 1,500 to 1,000,000.

Particularly suitable binders are xanthan gum, carboxymethyl cellulose, polyvinyl pyrrolidone and mixtures of these water-soluble polymers which may be present in a quantity of up to 1.0% by weight.

Suitable surfactants are, for example, sodium alkyl sulfates containing 12 to 18 carbon atoms in the alkyl group. These compounds also have an enzyme-inhibiting effect on the bacterial metabolism of tartar. Other suitable surfactants are alkali metal salts, preferably sodium salts of alkyl polyglycol ether sulfate containing 12 to 16 carbon atoms in the linear alkyl group and 2 to 6 glycol ether groups in the molecule, of linear alkane ($C_{12-18}$) sulfonate, of sulfosuccinic acid monoalkyl ($C_{12-18}$) esters, of sulfated fatty acid monoglycerides, sulfated fatty acid alkanolamides, sulfoacetic acid alkyl ($C_{12-16}$) esters, acyl sarcosines, acyl taurides and acyl isethionates containing 8 to 18 carbon atoms in the acyl group.

Ampholytic and zwitterionic surfactants, more particularly betaine surfactants, for example cocoalkyl betaine or cocoacylamidopropyl betaine, are also suitable. Finally, nonionic surfactants, for example ethoxylates of fatty acid mono- and diglycerides, of fatty acid sorbitan esters and alkyl (oligo)glucosides, may also be used.

In a particularly preferred embodiment, the tooth cleaning gels according to the invention contain a water-soluble binder and a surfactant combination of anionic, zwitterionic and nonionic surfactants as further ingredients.

Flavors and sweeteners are normally used for flavoring. Suitable flavors are, for example, peppermint oil, spearmint oil, eucalyptus oil, aniseed oil, fennel oil, caraway oil, methyl acetate, cinnamaldehyde, anethol, vanillin, thymol and other natural or nature-identical essential oils or even synthetic flavors.

Suitable sweeteners are, for example, saccharin sodium, acesulhpam, aspartame, sodium cyclamate, steviosides, thaumatine, sucrose, lactose, maltose or fructose, glycyrrhizin, etc.

Suitable scale inhibitors are, for example, organic phosphonates, such as azacycloheptane-2,2-diphosphonic acid disodium salt or 1-hydroxyethane-1,1-diphosphonic acid tetrasodium salt.

Suitable fluorine compounds are, for example, sodium fluoride and sodium monofluorophosphate ($Na_2PO_3F$).

The vitamins present may be selected, for example, from retinol, panthenol or a salt of pantothenic acid, ascorbic acid or salts or esters thereof or mixtures thereof. In a preferred embodiment, a combination of panthenol and retinol is present for improving the inflammation-inhibiting properties.

The tooth cleaning gels according to the invention may additionally contain typical toothpaste ingredients, for example buffering agents, for example primary, secondary or tertiary alkali metal phosphates, citric acid/sodium citrate, wound-healing and anti-inflammatory agents such as, for example, urea, allantoin, camomile-based active principles (azulene), alkali metal thiocyanate, acetylsalicylic acid derivatives, lower alcohols, for example ethanol or isopropanol, dyes and pigments, preservatives such as, for example, benzoic acid, sorbic acid and salts thereof, p-hydroxybenzoic acid esters.

The following Examples are intended to illustrate the invention.

EXAMPLES

Liquid tooth cleaning gels with the following composition were produced:

|  | 1 | 2 | 3 | 4 | 5 |
|---|---|---|---|---|---|
| Sident 12 SPLS | 12 | — | — | 12 | — |
| Sident 8 | — | 12 | 12 | — | — |
| Sorbosil AC 39 | — | — | — | — | 12 |
| Sorbitol (70%) | 30 | 30 | 70 | 75 | 30 |
| Glycerol (86%) | 33 | 33 | — | — | 33 |
| Lipoxol 1550 | 1 | 1 | 1.5 | — | 1.0 |
| Lipoxol 400 | — | — | — | 2.0 | — |
| Keltrol F | 0.33 | 0.5 | — | — | 0.5 |
| Cekol 2000 | — | — | 0.5 | 0.2 | — |
| $MgSO_4 7H_2O$ | 0.21 | 0.21 | 0.5 | 0.3 | 0.21 |
| $ZnSO_4 7H_2O$ | 0.16 | 0.16 | 0.16 | — | 0.16 |
| $MnSO_4 H_2O$ | 0.01 | 0.01 | — | — | 0.01 |
| Texapon K1296 | 1.5 | 1.5 | 1.5 | 1.5 | 1.5 |
| Tego Betain BL 215 | 0.6 | 0.6 | 0.6 | 0.6 | 0.6 |
| Tagat S | 0.5 | 0.5 | 0.5 | 0.5 | 0.5 |
| Hexetidine | 0.03 | 0.03 | 0.05 | 0.04 | 0.03 |
| Triclosan | — | — | — | — | 0.10 |
| NaF | 0.33 | 0.33 | — | — | 0.32 |
| $Na_2PO_3F$ | — | — | 1.1 | 1.0 | — |

-continued

|                | 1      | 2      | 3      | 4      | 5      |
|----------------|--------|--------|--------|--------|--------|
| Na$_2$HPO$_4$  | 0.2    | 0.2    | 0.2    | 0.2    | 0.2    |
| Na benzoate    | 0.5    | 0.5    | —      | —      | 0.5    |
| Na saccharinate| 0.2    | 0.2    | 0.2    | 0.2    | 0.2    |
| Flavoring oil  | 1.0    | 1.0    | 1.0    | 1.0    | 1.0    |
| Ethanol, dye   | 2.0    | 2.0    | 2.0    | 2.0    | 2.0    |
| Water          | to 100 | to 100 | to 100 | to 100 | to 100 |

The following commercial products were used:

Sident 12 SPLS (Degussa-Hüls):
  Precipitated silica, BET surface 80 m$^2$/g
Sident 8 (Degussa-Hüls):
  Hydrogel silica, BET surface 60 m$^2$/g
Sorbosil AC 39 (Degussa-Hüls):
  Precipitated silica
Lipoxol 1550 (RWE/DEA):
  Polyethylene glycol, molecular weight 1550
Lipoxol 400 (RWE/DEA):
  Polyethylene glycol, molecular weight 400
Keltrol F (Kelco):
  Xanthan gum
Cekol 2000 (Metsa):
  Sodium carboxymethyl cellulose, viscosity (2%, 25C): 1.3–2.3 Pa·s
Texapon K 1296 (Cognis Deutschland):
  Sodium lauryl sulfate (powder),
Tego Betain BL 215 (Goldschmidt):
  Fatty acid amidoalkyl betaine (30%), Cocoamidopropyl Betaine
Tagat S (Goldschmidt):
  PEG 30 Glyceryl Stearate

What is claimed:

1. A water-based liquid tooth cleaning gel with a viscosity below 50 Pa·s (20° C.), comprising

| | |
|---|---|
| 10 to 20% by weight of | a silica polish, |
| 40 to 60% by weight of | a humectant selected from the group consisting of sorbitol, glycerol, polyethylene glycol and mixtures thereof, |
| 0.01 to 0.2% by weight of | magnesium in the form of a dissolved salt and |
| 0.01 to 1% by weight of | an antimicrobial 5-aminohexahydropyrimidine |

2. The liquid tooth cleaning gel of claim 1, wherein a water-soluble binder and a surfactant combination of anionic, zwitterionic and nonionic surfactants are additionally present.

3. The liquid tooth cleaning gel of claim 2, wherein a binder selected from the group consisting of xanthan gum, carboxymethyl cellulose, polyvinyl pyrrolidone or mixtures of these water-soluble polymers is present in a quantity of up to 1% by weight.

4. The liquid tooth cleaning gel of claim 1 wherein the silica polish is selected from the group consisting of silica gels, silica hydrogels and precipitated silicas.

5. The liquid tooth cleaning gel of claim 3 wherein the water content is from 25 to 35% by weight.

6. The liquid tooth cleaning gel of claim 1 wherein the magnesium is introduced into the liquid tooth cleaning gel in the form of MgSO$_4$.7H$_2$O.

7. The liquid tooth cleaning gel of claim 1 wherein the 5-aminohexahydropyrimidine is 1,3-bis-(2-ethylhexyl)-5-methyl-5-amino-hexahydropyrimidine.

8. The liquid tooth cleaning gel of claim 1 wherein the humectant consists of a mixture of sorbitol(a), glycerol(b) and polyethylene glycol(c) in a ratio by weight of (a) to (b) to (c) of 10:(0–8): (0.2–2).

9. The liquid tooth cleaning gel of claim 1, wherein a binder selected from the group consisting of xanthan gum, carboxymethyl cellulose, polyvinyl pyrrolidone or mixtures of these water-soluble polymers is present in a quantity of up to 1% by weight.

* * * * *